United States Patent [19]

Borden

[11] Patent Number: 4,783,599
[45] Date of Patent: Nov. 8, 1988

[54] PARTICLE DETECTOR FOR FLOWING LIQUIDS WITH THE ABILITY TO DISTINGUISH BUBBLES VIA PHOTODIODES DISPOSED 180° APART

[75] Inventor: Peter G. Borden, Palo Alto, Calif.

[73] Assignee: High Yield Technology, Mountain View, Calif.

[21] Appl. No.: 12,976

[22] Filed: Feb. 10, 1987

[51] Int. Cl.⁴ .......................................... G01N 15/07
[52] U.S. Cl. .................... 250/574; 356/341; 250/575
[58] Field of Search ................ 250/574, 575; 356/336, 356/338, 341, 342, 343

[56] References Cited

U.S. PATENT DOCUMENTS

| | | | |
|---|---|---|---|
| 3,705,771 | 12/1972 | Friedman et al. | 356/342 |
| 3,785,735 | 1/1974 | Friedman et al. | 356/342 |
| 3,797,937 | 3/1974 | Shofner | 356/336 |
| 4,078,863 | 3/1978 | Eriksson et al. | 356/336 |
| 4,188,121 | 2/1980 | Hirleman, Jr. et al. | 356/343 |
| 4,193,692 | 3/1980 | Wynn | 356/343 |
| 4,507,556 | 3/1985 | Brenholdt | 356/338 |
| 4,595,291 | 6/1986 | Tatsuno | 356/343 |

Primary Examiner—David C. Nelms
Assistant Examiner—William L. Oen
Attorney, Agent, or Firm—Nathan N. Kallman; Alan H. MacPherson; Richard Franklin

[57] ABSTRACT

A system for detecting contaminant particles in a liquid, such as used for processing wafers during the manufacture of integrated circuits, distinguishes non-contaminant bubbles generally found in liquids from contaminant particles. The system provides a controlled laminar fluid flow of the liquid through a pipe, and the substantially spherical bubbles in the flow path are detected by symmetrically spaced photodiodes. The irregularly shaped contaminant particles are detected, whereas the presence of bubbles are negated by the detection system by virtue of the balanced photodiode assembly.

11 Claims, 3 Drawing Sheets

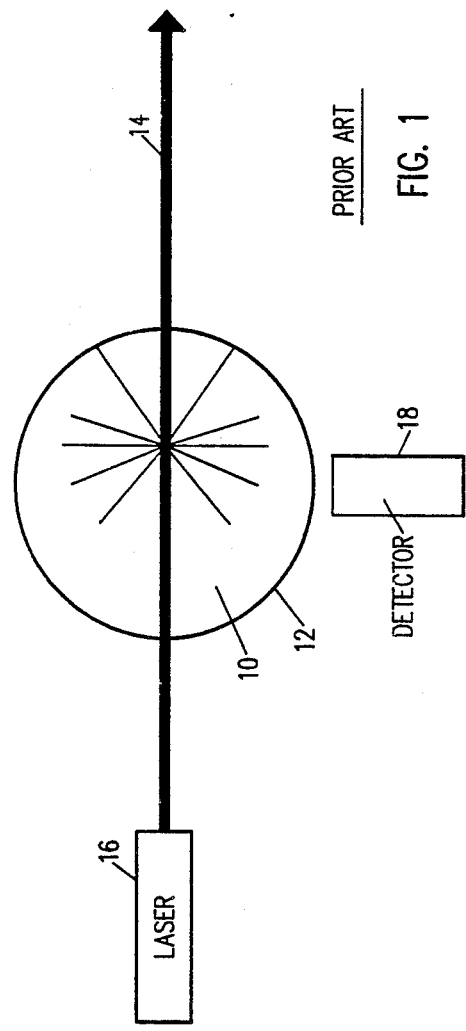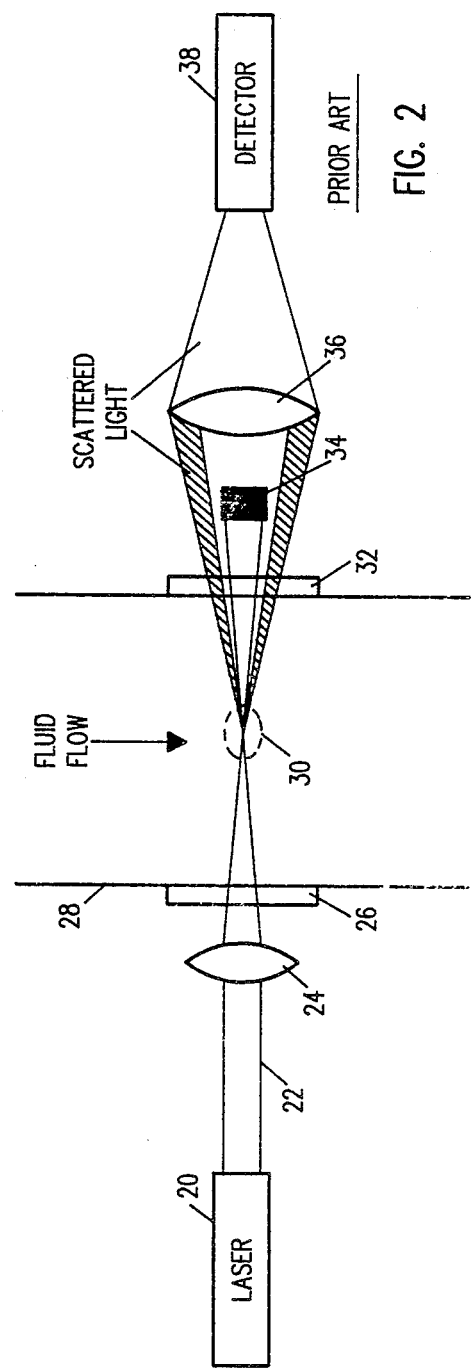

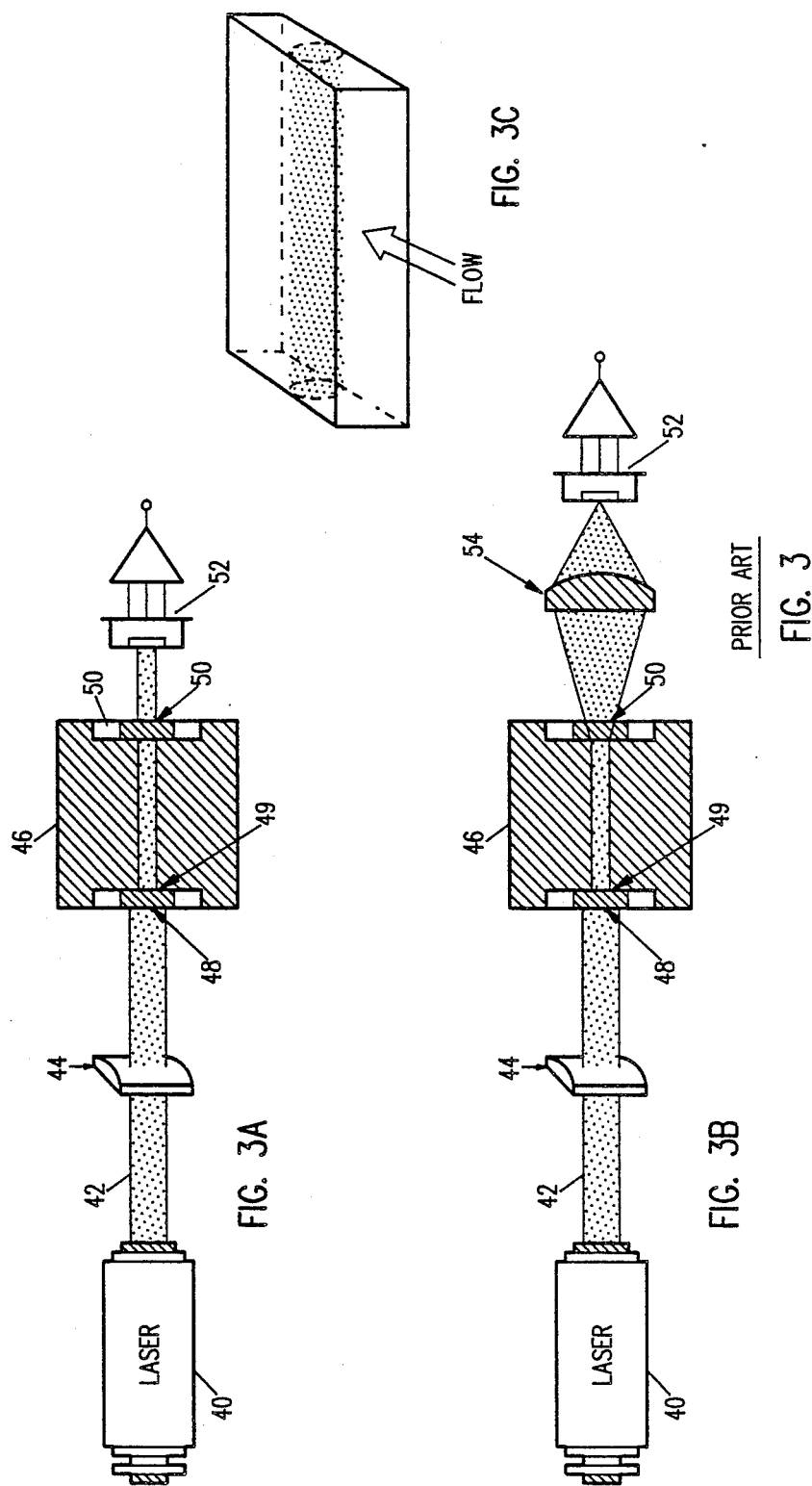

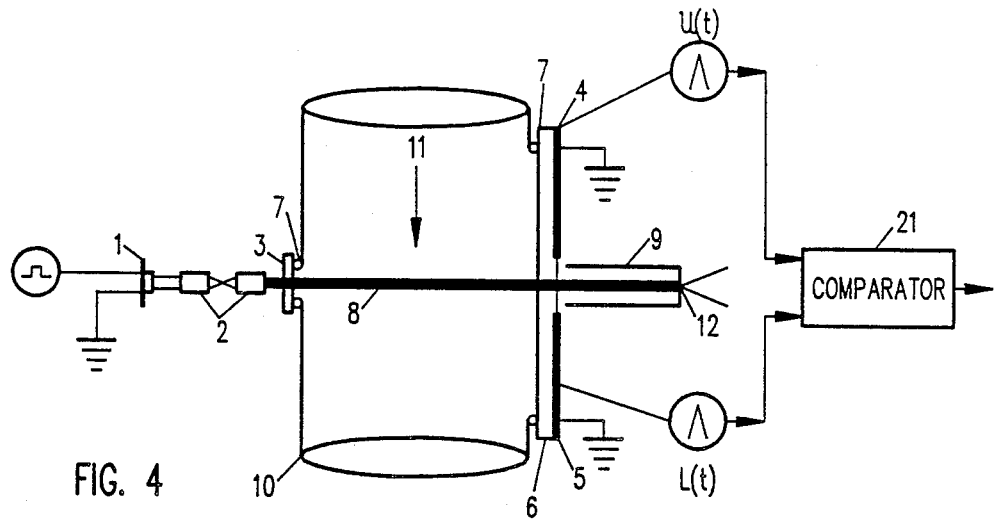
FIG. 4
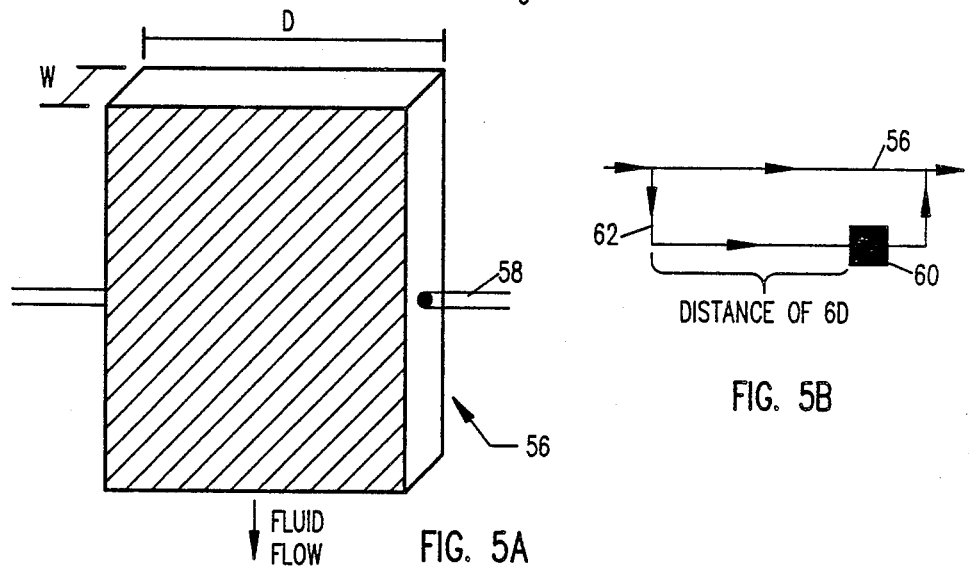
FIG. 5A
FIG. 5B
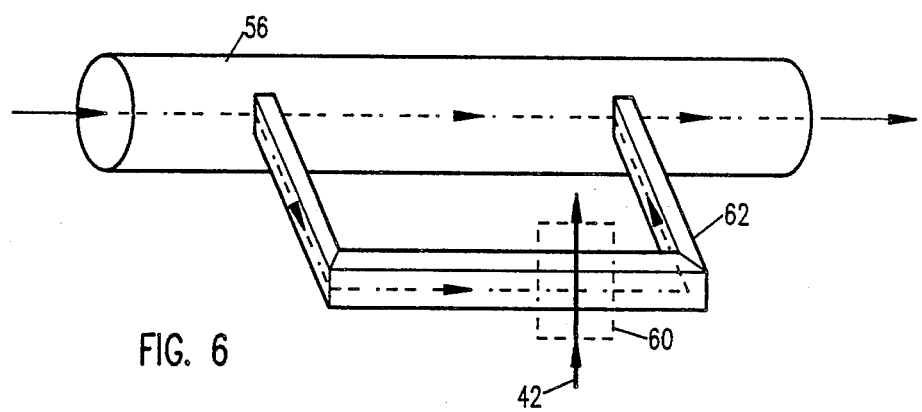
FIG. 6

PARTICLE DETECTOR FOR FLOWING LIQUIDS WITH THE ABILITY TO DISTINGUISH BUBBLES VIA PHOTODIODES DISPOSED 180° APART

BACKGROUND OF THE INVENTION

1. Field of the Invention

This invention relates to a particle detection system and in particular to a detection system for distinguishing noncontaminant bubbles of a liquid from contaminant particles in the liquid.

2. Description of the Prior Art

During the processing of semiconductor wafers and the manufacture of integrated circuits, various liquids, such as HF, for example, are used for etching patterns in the wafers, and various solvents, such as isopropyl alcohol, TCE (trichloroethylene) and deionized water, are used to clean the wafers. During the etching or cleaning processes, contaminant particles in these fluids may be deposited on the wafers. The appearance of such particles significantly reduces the yield of the integrated circuits in production, particularly those circuit designs having very fine dimensions.

Various prior art devices have been employed to monitor particles in liquids. One prior art apparatus is shown in FIG. 1, wherein a liquid 10, which is drawn from a bath or pipe, is placed in a sample bottle or container 12. The bottle is then scanned with a laser beam 14 derived from a laser source 16, and the light is scattered from the particles on which it impinges in the liquid sample. The scattered light is detected by a detector 18. This arrangement is characterized by a number of problems. One problem is that the measurement is difficult and tedious to accomplish because it is not in situ. Also, since the sample is handled during the measurement process, additional contaminants may be introduced into the sample. Furthermore, the laser beam that passes through the bottle tends to become distorted thus leading to a loss of sensitivity of the detection system.

Another approach to detection of contaminant particles is shown in FIG. 2, wherein an airborne particle counter that allows measurement in situ employs a laser 20 for providing a laser beam 22 which is focused by means of a lens 24 through a window 26 of a small pipe section 28. The focused laser beam impinges on a sample volume 30 which is obtained from a fluid flowing through the pipe so that contaminant particles in the fluid can be detected. The beam and the light scattered by the particles passing through the beam exit from the pipe through a second window 32. As the scattered light is relatively very weak, the main beam which would normally saturate the detector is blocked by a stop element 34. The scattered light is focused through a lens 36 onto a detector 38. A problem which exists with this arrangement is that the focal spot of the laser is very small, generally less than a cubic millimeter, and therefore only a small fraction of the particles distributed in the liquid can be detected.

In another prior art arrangement, such as illustrated in FIGS. 3A and 3B a collimated laser beam 42 is derived from a laser source 40, which may be a helium-neon laser. The beam is passed through a cylinder lens 44 and through a window 48 associated with a container or cell 46 through which the sample liquid is passed. The window includes a beam truncating aperture 49 which narrows the beam to a desired diametric dimension. In the extinction mode, which is represented by FIG. 3A, the beam passes through an exit window 50 and the intensity of the beam is measured by means of a photodiode and preamplifier circuit 52. The extinction mode is used for the measurement of large contaminant particles. To measure the smaller particles, a scattering mode such as shown in FIG. 2 is employed where the main beam is blocked. For the measurement of smaller particles in the scattering mode, a collecting lens 54 is interposed between the exit window 50 and the photodiode and preamplifier circuit 52, as depicted in FIG. 3B.

In all of these prior art systems, there is an inability to distinguish the bubbles normally found in liquids from contaminant particles. With a small particle, the light of the beam is scattered because the index of refraction of the particle is different than that of the liquid medium. Similarly, the index of refraction of a bubble, which is about 1.0, differs from that of the surrounding fluid, which is typically 1.3 to 1.5. Consequently, a bubble will appear to the detectors of the prior art systems as an undesirable contaminant particle. However, a bubble is not deemed to be a contaminant, since it could pass through a filter which is used to stop contaminants. Therefore, to ascertain the accurate contamination level in a fluid, it is necessary to distinguish bubbles within a liquid from that of contaminant particles.

SUMMARY OF THE INVENTION

A system for detecting contaminant particles in a liquid and for distinguishing bubbles from contaminant particles employs symmetrically spaced photodiodes that detect irregularly shaped particles as contaminants and spherically shaped bubbles as noncontaminants.

DESCRIPTION OF THE DRAWINGS

The invention will be described with reference to the drawings in which:

FIG. 1 is a representational view of a prior art particle detection system;

FIGS. 2, 3A and 3B are schematic views of prior art particle detection systems;

FIG. 3C is a representational view of a laser beam transverse to particle flow;

FIG. 4 is a schematic view of a particle detector, in accordance with this invention;

FIGS. 5A and 5B illustrates a specific embodiment of the invention; and

FIG. 6 depicts the relationship of a main pipe and shunt pipe, which are shown in FIG. 5B.

Similar numerals refer to similar elements throughout the drawing.

DETAILED DESCRIPTION OF THE INVENTION

A detection system that is capable of distinguishing bubbles in a liquid from contaminant particles, in accordance with this invention, is illustrated in FIG. 4. When operating the system, bubbles in a liquid flow 11 pass through a collimated laser beam 8. The beam is formed with a laser diode 1 having a peak power of about 10 milliwatts at a wavelength of approximately 780 nanometers. The beam is passed through two gradient index lenses 2, the first having a pitch of about 0.29 and the second lens having a pitch of about 0.23. The laser beam passes through the diameter of a pipe section 19 entering through a window 3 and exiting through a window 6. The windows are sealed to the pipe 19 by seals 7, which may be O-rings or made from an adhesive material. The beam is terminated with a beam stop tube 9, which includes a photocell 13 that monitors the beam current to verify that the beam is at a desired correct power level.

According to this invention, a pair of silicon photodiodes 4 and 5 detect the scattered light formed by the impingement of the beam on the particles and the bubbles within the fluid flow. The photodiodes are bonded to the window 6 with an optical cement. The photodiode 4 is located above the beam and produces a signal designated as U(t), whereas photodiode 5 is situated below the beam and produces a signal designated as L(t). The photodiodes 4 and 5 are positioned substantially symmetrically above and below the beam path as it exits through the window 6.

When a bubble passes through the beam, the peak values of the signals U(t) and L(t) will be approximately equal. In contrast, when an irregularly shaped particle is in the path of the beam, the peak values of the signals U(t) and L(t) will not be equal. The peak values of the signals are compared in a comparator 21 which provides an output signal representing contaminant particles that traverse the beam. The signals that are derived from the passage of bubbles past the beam are effectively negated because the peak signal values of the U(t) and L(t) detected signals fed to the comparator 21 are substantially equal and balance out. Therefore, the output signal from the comparator represents the differential signal between the signal components generated by the scattered light received by the photodiodes from the irregularly shaped contaminant particles.

In the preferred implementation of this invention, the laser beam is preferably modulated, typically at a frequency of about 100 kiloHerz, by driving the laser diode with a square wave. The modulation serves to minimize sensitivity to background noise. In addition, a bandwidth of about 10 Hertz about the baseband is filtered out so that DC response is effectively removed. In this manner, the system is sensitive only to moving contaminant particles, and the sensitivity to defects or dirt on the windows that may scatter light is minimized. Also the effects of stray light are virtually eliminated.

The novel system provides improved detection of contaminants in corrosive liquids. When corrosive liquids are being monitored, the walls of the pipe through which the sample is passed is preferably coated with Teflon (a trademark of Dupont), and the windows are made of a plastic, or are coated with silicon nitride which is resistant to etching by hydrofluoric acid. Another feature that is available with a system of this type is the use of reflective walls in the pipe, so that additional forward scattered light is channeled to the photodiodes thereby increasing the response.

With reference to FIGS. 5A, 5B and FIG. 6, a specific implementation of the invention incorporates a pipe having a predetermined shape to ensure proper fluid flow. In FIG. 5A, the dimensions of the width W and length D are represented, and the ratio of D/W is made to be less than 10 in this embodiment. It is preferable that the width W should be no greater than 2 millimeters to allow a collimated laser beam to traverse the width of the pipe. Thus, the length dimension D is less than 2.0 centimeters. With these dimensions, a fully developed turbulent flow occurs causing the contaminant particles to move in a straight path down the pipe without being subjected to pressure gradients or a swirling flow. In order to ensure that a proper flow is established, the sensor or detector 60 should be at a distance of at least 6D along the pipe section in the direction of flow. As depicted in FIG. 5B, and FIG. 6, a shunt pipe 62 is connected to the main flow pipe 56 to allow a sampling of the main flow, whereby larger volume flows can be monitored. As represented in FIG. 6, the cross-sectional area of the main pipe 56 is much larger than the cross-sectional area of the shunt pipe 62.

By means of the novel detection system, bubbles that are substantially spherical, which are found in liquids, are not sensed as contaminant particles during detection in a liquid particle detector. The forward scattering of light that results by an impingement of the laser beam on the symmetrical bubbles is substantially symmetrical above and below the beam so that the scattered light appearing at the photodiodes are substantially equal in intensity whereby the signals generated by the photodiodes are equal in value. In contrast, the asymmetrical solid contaminant particles provide forward scattering light that varies according to the shape of each particle that passes through the projected beam. The irregulary shaped particles cause different peak intensity signals U(t) and L(t) to be generated, resulting in a differential signal that is produced by the comparator or difference amplifier 21.

What is claimed is:

1. A system for detecting contaminant particles in a liquid and for distinguishing bubbles from the contaminant particles comprising:
   means for providing a flow of liquid to be monitored;
   means for directing a light beam along an optical axis path through said liquid so that light is scattered when said beam impinges on a particle or a bubble in said liquid;
   means for detecting said scattered light comprising first and second photodiodes that are disposed symmetrically about said optical axis path about 180° relative to each other, respectively on each side of said light beam path, said photodiodes being equally spaced from the path of said light beam for generating respective signals representing the intensity of the scattered light detected by said photodiodes; and
   means for comparing said signals so that a difference signal is produced which is indicative of the presence of contaminant particles, and the signals generated by detecting bubbles in said liquid are effectively negated.

2. A system as in claim 1, wherein said light beam comprises a collimated laser beam.

3. A system as in claim 2, wherein said laser beam has a peak power of about 10 milliwatts at a wavelength of about 780 nanometers.

4. A system as in claim 2, wherein said laser beam is modulated with a square wave signal at a frequency of about 100 kiloHerz for minimizing sensitivity to background noise.

5. A system as in claim 1, including a plurality of gradient index lenses through which the light beam is passed.

6. A system as in claim 1, including a main pipe through which said liquid flow is passed, and a shunt pipe connected to said main pipe for sampling the liquid that passes through the main pipe.

7. A system as in claim 6, wherein the ratio of the length to the width of said main pipe is less than 10.

8. A system as in claim 7, wherein the length of said main pipe is less than 2 centimeters and the width of said main pipe is less than 2 millimeters.

9. A system as in claim 6, including windows adjacent to said main pipe through which said light beam enters and exits said main pipe.

10. A system as in claim 1, wherein said beam is terminated by a beam stop for verifying that the power level of the beam is at a desired level.

11. A system as in claim 1, wherein the signals being compared are peak signals generated in response to the detected scattered light.

* * * * *